(12) United States Patent
Benzon

(10) Patent No.: US 9,883,929 B2
(45) Date of Patent: Feb. 6, 2018

(54) DENTAL SUPERSTRUCTURE, AND METHOD OF MANUFACTURE THEREOF

(71) Applicant: Kulzer GmbH, Hanau (DE)

(72) Inventor: Sture Benzon, Helsingborg (SE)

(73) Assignee: Kulzer Gmbh, Hanau (DE)

(*) Notice: Subject to any disclaimer, the term of this patent is extended or adjusted under 35 U.S.C. 154(b) by 428 days.

(21) Appl. No.: 14/488,870

(22) Filed: Sep. 17, 2014

(65) Prior Publication Data

US 2015/0005918 A1     Jan. 1, 2015

Related U.S. Application Data

(62) Division of application No. 12/438,692, filed as application No. PCT/SE2007/005066 on Aug. 22, 2007, now abandoned.

(30) Foreign Application Priority Data

Aug. 25, 2006    (SE) ...................................... 0601755

(51) Int. Cl.
     *A61C 13/00*      (2006.01)
     *A61C 8/00*      (2006.01)
     *G05B 15/02*      (2006.01)

(52) U.S. Cl.
     CPC ........ *A61C 13/0004* (2013.01); *A61C 8/0048* (2013.01); *A61C 8/0051* (2013.01); *A61C 13/0009* (2013.01); *A61C 13/0022* (2013.01); *G05B 15/02* (2013.01); *A61C 8/0068* (2013.01)

(58) Field of Classification Search
CPC ............ A61C 13/0004; A61C 13/0022; A61C 8/0048; A61C 8/0051; A61C 13/0009; A61C 8/0068; A61C 13/0013; G05B 15/02
See application file for complete search history.

(56) References Cited

U.S. PATENT DOCUMENTS

| | | |
|---|---|---|
| 4,931,016 A | 6/1990 | Sillard |
| 4,968,250 A | 11/1990 | Small |
| 5,015,186 A | 5/1991 | Detsch |
| 5,116,225 A | 5/1992 | Riera |
| 5,630,717 A | 5/1997 | Zuest et al. |
| 5,725,376 A | 3/1998 | Poirier |
| 5,885,078 A | 3/1999 | Cagna et al. |

(Continued)

FOREIGN PATENT DOCUMENTS

| | | |
|---|---|---|
| EP | 0 419 431 | 3/1991 |
| EP | 0 580 945 | 2/1994 |

(Continued)

OTHER PUBLICATIONS

International Search Report for International Application No. PCT/SE2007/050566 dated Nov. 27, 2017 (6 pages).

(Continued)

*Primary Examiner* — Jun Yoo
(74) *Attorney, Agent, or Firm* — Merchant & Gould P.C.

(57) ABSTRACT

A dental superstructure with integrated spacers including a main body and at least one integrated spacer. The superstructure is intended to be connected to the at least one osseointegrated dental implant through connection between the integrated spacer and the osseointegrated dental implant. A manufacturing method thereof is also provided.

7 Claims, 2 Drawing Sheets

(56) References Cited

U.S. PATENT DOCUMENTS

| | | | |
|---|---|---|---|
| 5,947,733 | A | 9/1999 | Sutter et al. |
| 6,227,859 | B1 | 5/2001 | Sutter |
| 6,250,924 | B1 | 6/2001 | Luotio |
| 6,283,753 | B1 | 9/2001 | Willoughby |
| 6,319,000 | B1 | 11/2001 | Branemark |
| 6,382,975 | B1* | 5/2002 | Poirier ............... A61C 1/084 433/173 |
| 6,666,684 | B1 | 12/2003 | Names |
| 6,788,986 | B1* | 9/2004 | Traber ............... A61C 8/0048 433/201.1 |
| 6,848,908 | B2 | 2/2005 | Bjorn et al. |
| 7,322,824 | B2 | 1/2008 | Schmitt |
| 7,901,209 | B2* | 3/2011 | Saliger ............... A61C 8/0048 433/215 |
| 2005/0037320 | A1* | 2/2005 | Poirier ............... A61C 1/084 433/173 |
| 2005/0115368 | A1 | 6/2005 | Prager et al. |
| 2006/0093988 | A1* | 5/2006 | Swaelens ............ A61C 1/084 433/76 |

FOREIGN PATENT DOCUMENTS

| | | |
|---|---|---|
| EP | 0 987 994 | 12/2005 |
| GB | 1 201 856 | 8/1970 |
| KR | 2001 0091658 | 10/2001 |
| KR | 2006 0012036 | 2/2006 |
| SE | 506 850 | 2/1998 |
| WO | WO 96/25120 | 8/1996 |
| WO | WO 98/47441 | 10/1998 |
| WO | WO 01/70127 | 9/2001 |

OTHER PUBLICATIONS

Balaji. "Textbook of Oral Maxillofacial Surgery: Section IV: Minor Oral Surgical Procedures." *Elsevier India*. 2007 pp. 311-315.

Heasman. "Second Edition: Master Dentistry: vol. 2: Restorative Dentistry, Pediatric Dentistry and Orthodontics." *Churchill Livingston El Sevier*. 2003. pp. 133.

Hellden et al. "The Cresco FPD and Implant Concept: Presentation of a Technology for Fabrication of Abutment-Free, Passively Fitting Superstructures." *International J. of Periodontics & Restorative Dentistry*. vol. 25. Nov. 1, 2005. pp. 2-8.

Malik. "$2^{nd}$ Edition: Textbook of Oral and Maxillofacial Surgery." *Jaypee Brothers Medical Publishers (P) Ltd* 2008. pp. 745-746.

Misch. "Contemporary Implant Dentistry: Third Edition." *Mosby El Sevier*. 2008. pp. 31-32.

Misch. "Dental Implant Prosthetics." *El Sevier Mosby*. 2005. pp. 37-38.

Ortorp et al. "Clinical experiences with laser-welded titanium frameworks supported by implants in the edentulous mandible: a 5-year follow-up study." *Int. J. Prosthodont*. vol. 12. No. 1. 1999. pp. 65-72.

Ortorp et al. "Comparisons of precision f fit between cast and CNC-milled titanium implant frameworks for the dentulous mandible." *Int. J. Prosthodont*. vol. 16. No. 2 2003. pp. 194-200.

Ortorp et al. "Photogrammetry and Conventional Impressions for Recording Implant Positions: A Comparative Laboratory Study." *Clinical Implant Dentistry & Related Research*. vol. 7. I. 1. 2005. pp. 43-50.

Ortorp et al. "Screw Preloads and Measurements of Surface Roughness in Screw Joints: An Invitro Study on Implants Frameworks." *Clinical Implant Dentistry & Related Research*. vol. 7. I.3. 2005. pp. 141-149.

Ortorp. "On titanium frameworks and alternative impression techniques in implant dentistry." *The Sahlgrenska Academy at Goteborg University*. 2005. pp. 1-88.

Ortorp. "Clinical Experiences of Computer Numeric Control-Milled Titanium Frameworks Supported by Implants in the Edentulous Jaw: A 5-Year Prospective Study." *Clin. Implant Dentistry R. Res*. vol. 6. No. 4. 2004. pp. 199-209.

* cited by examiner

DENTAL SUPERSTRUCTURE, AND METHOD OF MANUFACTURE THEREOF

This application is a Division of U.S. Ser. No. 12/438,692, filed 23 Aug. 2010, which is a National Stage Application of PCT/SE2007/050566, filed 22 Aug. 2007, which claims benefit of Serial No. 0601755-2, filed 25 Aug. 2006 in Sweden and which applications are incorporated herein by reference. To the extent appropriate, a claim of priority is made to each of the above disclosed applications.

FIELD OF THE INVENTION

This invention pertains in general to the field of a dental superstructure and a manufacturing method of said superstructure. More particularly the invention relates to a superstructure to be connected to an osseointegrated dental implant. A superstructure of this kind is disclosed in SE506850.

BACKGROUND OF THE INVENTION

The goal of a dental implant is to restore the patient to normal function, comfort, aesthetic, speech and health regardless of the current oral condition. This is obtained by dental implants in combination with superstructures and separate spacers. In this respect, the use of biocompatible titanium started in Sweden as early as 1950, and has since then been further developed and spread world-wide. During the 1980's a number of implant systems entered the world market.

These implant systems are based on the implantation of dental implants, such as dental implants made of the above mentioned biocompatible titanium, through insertion into the patient's jawbone. Healing spacers are then applied on the implants. These healing spacers are left during a period of time of 2 to 6 months, during which period of time osseointegration and healing of soft tissue takes place. During the healing period the gum, i.e. the soft tissue, is shaped after the healing spacers. After the healing period the healing spacers are removed and the dental superstructure is applied to the implants via separate spacers. These spacers are typically not of the same shape as the healing spacers, i.e. not shaped individually, and often even mass-produced. Thus, a bad matching between the superstructure and the spacers, and thereby the gum tissue is obtained. This results in an uneven attachment of the superstructure in respect of the gum. Thus, a bad fit, such as a gap, etc., between the gum and the superstructure is formed. The use of separate spacers also increases the time and complexity of the application of the dental superstructure to the implants. Also, the manufacturing and assembling of the different parts, such as the dental implant, superstructure, spacers etc., makes the process expensive and time consuming, resulting in an increased economic loss and prolonged period of time from the initiation to the termination of the implantation process.

A bad fit of the gum to the dental superstructure is aesthetically unpleasing and allows for example food debris to accumulate in the pocket between the superstructure and the gum tissue. Bacteria may also accumulate in the interface between the dental structure and the separate spacers, causing problems with odour and hygiene in the oral cavity.

SE506850 discloses a dental prosthesis system incorporating a superstructure and fixtures that are implantable in a person's jawbone. Each fixture is anchored in the jawbone and its opposite end is arranged so that it will be possible to attach the superstructure to it.

Different spacers, upon which spacers a superstructure may be applied, are known in the art. For example may the spacers described in EP 0987994, EP 0419431, and EP 0580945, be mentioned. Commercially available spacers can only be obtained in a limited number of heights, which is a drawback with the prior art technology.

WO 98/47441 discloses a system comprising a bar (3) for attaching the prosthesis, which is flush fitted between spacer elements, such as extensions (4), which spacer elements in turn are connected to the implant screws (6).

U.S. Pat. No. 6,283,753 describes dental abutment systems comprising a base that is adapted to mount in nonrotating fashion on any desired dental implant, root form or blade, from any supplier, together with a fixation screw which secures the base to the implant. Also, a core to which an abutment is cast in customized shape and form as desired is attached to the base and secured with an appropriate antirotational mechanism.

Thus, there is a need for a new superstructure that provides a good fit of the superstructure to the gum. There is also need for a simpler, faster and cheaper production method of dental superstructures. Furthermore, there is a need to provide for the possibility of a simple assembly ex situ (outside the patient's mouth) and application in situ (in the patient's mouth).

Hence, an improved superstructure would be advantageous, and in particular a superstructure allowing for a good fit of the superstructure to the gum. Furthermore, a simpler, faster and cheaper production method of said superstructure, cost-effectiveness, and/or a more simple assembly would be advantageous.

SUMMARY OF THE INVENTION

Accordingly, the present invention seeks to mitigate, alleviate or eliminate one or more of the above-identified deficiencies and to provide an improved superstructure of the kind referred to, and a manufacturing method thereof. For this purpose the superstructure is characterized by at least one integrated spacer, such that said spacer, in use, is providing space between a main body and a dental implant and cooperates with said dental implant, and the manufacturing method thereof is characterized by specifying information from said stereo-data, in form of position, dimension, angle, and/or shape of said at least one spacer, communicating said information and/or stereo-data to a computer, and shaping said dental superstructure from coordinate combinations calculated by said computer.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on embodiments of the present invention applicable to a superstructure, and also to a method of manufacturing said superstructure.

Figure 1:
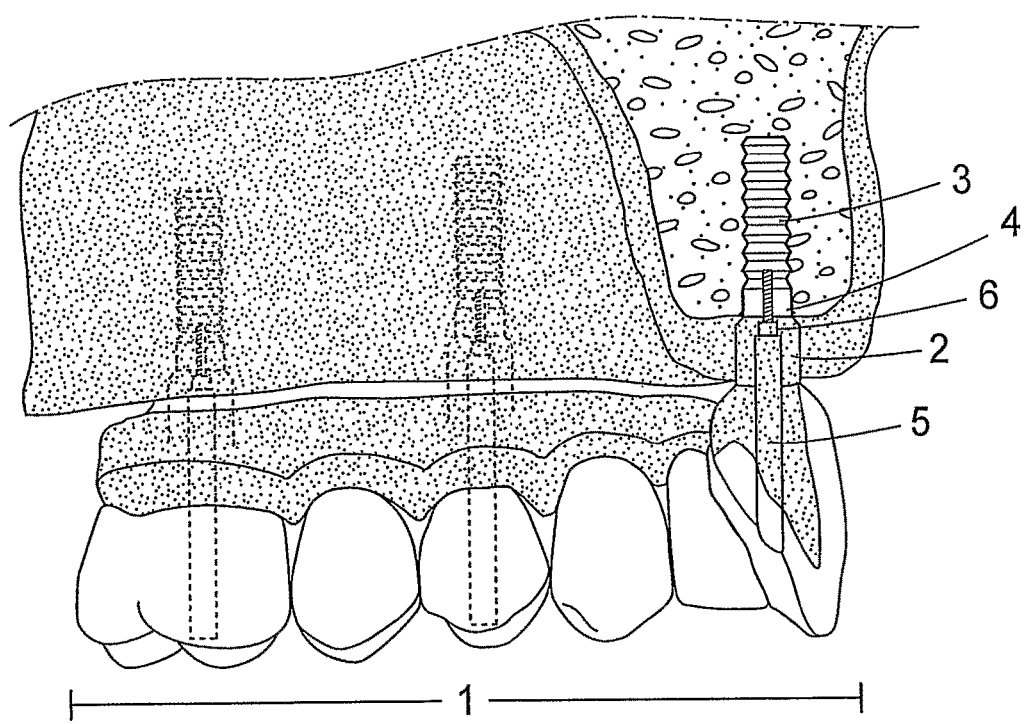
FIG. 1 illustrates an embodiment of a superstructure according to the present invention.

In one embodiment, according to FIG. 1, the present invention relates to a dental superstructure with a main body 1 and at least one integrated spacer 2 for replacement structure in human body parts, such as the jaw. The dental superstructure with integrated spacers is milled from one single-piece blank, such that the dental superstructure obtains a main body 1 and at least one spacer 2, wherein said main body and said at least one spacer are integrated. In this context the term integrated means that the dental superstructure, comprising a main body, and the at least one spacer are comprised in one piece of material, such that no interface is present in between said main body 1 of the superstructure and said at least one spacer 2. In this superstructure the dimensions of the at least one spacer 2 can be varied in accordance with the specific dental situation of a patient intended to receive said replacement structure. Thus, when a plurality of spacer elements 2 are integrated in said superstructure the spacers 2 may be dimensioned individually. When the superstructure is applied, the spacer(s) 2 will be cooperating with dental implants 3, inserted and/or osseointegrated in bone tissue. The cooperation is such that the superstructure may be fixed to the dental implants 3 through said spacer(s) 2 via a cooperation end 4. This may be obtained by providing the superstructure with integrated spacer(s) 2 with a recess 5 extending through the integrated spacer(s), in which recess 5 a screw may be inserted and screwed into the dental implant 3. In the cooperation end 4 a seat 6 for the screw may be provided. This seat may be provided with a hole, corresponding to the diameter of the threaded part of said screw, through which the integrated spacer(s) 2 may be attached with to dental implant 3 by said screw. Thus, a screw may be inserted in the superstructure and screwed into the dental implant, whereby the dental superstructure may be fixed to said dental implant 3. To obtain a perfect fit, i.e. no gap, between the superstructure and the gum tissue, the length and angle, in respect of the jawbone, superstructure, and jawbone, of the spacer(s) 2 will be individual for each spacer in respective spacer position.

Figure 2A:
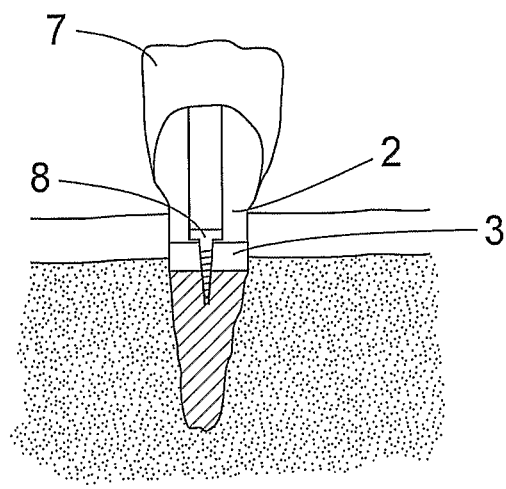
FIG. 2a illustrates an embodiment of a superstructure having a facing material thereon.

It is possible to provide a facing material 7 on said superstructure with integrated spacer(s) 2, in accordance with FIG. 1 or FIG. 2a, which facing material 7 emulates the appearance of real teeth. The application of a facing material 7 on the superstructure may be performed after the superstructure has been mounted on the dental implant 3. This may for example be done by cementing, or by the aid of any other suitable adhesive. Thus, the screw hole in the superstructure, for receiving a screw 8 for fastening the superstructure to the dental implant, may not be accessible from the outside of the superstructure after the superstructure has been fixated to the dental implant 3. This facing material 7 may be selected from the group consisting of ceramics and high-strength ceramics, porcelain, and silica-based porcelains.

Figure 2B:
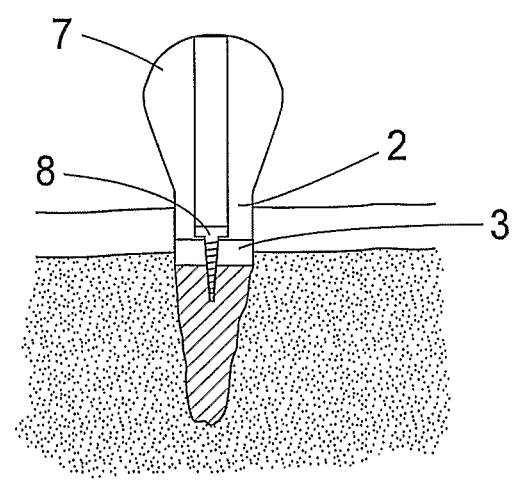
FIG. 2b illustrates an embodiment of a superstructure made of a facing material.

According to another embodiment, according to FIG. 2b, of the present invention, the superstructure with integrated spacer (s) 2 is manufactured in a facing material 7 with the appearance of natural teeth, or the facing material is applied such that the facing material does not cover the screw channel. Thereby, no application of a facing material 7 is necessary. Thus, the screw hole in the superstructure, for receiving the screw 8 for fastening the superstructure to the dental implant 3, may be accessible from the outside of the superstructure after the superstructure has been fixated to the dental implant 3. The screw hole may then be covered with a plug after the fixation, which plug may be removed if there is a need for a follow-up draft of the screw 8.

According to one embodiment a dental implant, for example made of biocompatible titanium, is first inserted at the location of a removed tooth. Then healing spacers are applied on the implants. These healing spacers are left in that position until a satisfactory osseointegration of the dental implant and healing of the gum tissue has been obtained. The dental situation of the patient is then obtained, by using identification systems and/or equipment for determining three-dimensional structure, such as stereophotography, scanning of the outer form, etc. It is also possible to obtain a manual imprint of the dental situation when the healing spacers are in place. This manual imprinting may for example be obtained by applying a fast curing material, known in the art, on the gum and teeth, whereby an imprint of the dental situation is obtained. This imprint may then be used to obtain the correct information, such as coordinates and/or dimensions and angles, in respect of the positioning of spacer(s).

In one embodiment of the present invention the dental situation of the patient is obtained without the use of healing spacers, i.e. the dental situation is obtained after or before the insertion of the dental implant, by any of the methods described above.

The scanning of the outer form can be performed using scanning needles, optical light beams, etc., in order to attain a better fit of the dental superstructure to the patients mouth, especially, gum shape at the implant site. The skilled artisan in the field of determining three-dimensional structures knows these techniques.

In this way the correct information, such as coordinates and/or dimensions and angles, in respect of the positioning of spacer(s) is obtained. This information may then be transferred to a computer. The transfer of information from the identification systems to the computer may be performed manually, such as typing, or digitally, such as by a computer readable medium or direct communication between the identification system and said computer.

The computer may calculate a coordinate combination that is specific for the dental situation of the patient, based on the spatial information. The computer may comprise memory equipment and CPU, which receives and stores, and, respectively, processes the received information. With the aid of the information, the appearance of the superstructure can be simulated, for example on a computer screen. By interaction with a user, the simulated superstructure may be shaped in a known manner.

This coordinate combination, such as digital coordinate combination, may then be used to instruct a mill, or any other suitable shaping equipment, how to perform the shaping, such as milling, of the superstructure. Thus, the superstructure may be shaped, such as milled, from a single-piece blank with integrated spacer(s).

In one embodiment said shaping is performed by moulding.

The material of said single-piece blank, which is used to manufacture the superstructure with integrated spacer(s), may in one embodiment of the present invention be selected from the group comprising titanium, zirconium oxide, alloys of titanium and zirconium, titanium alloys, zirconium alloys, cobalt-chromium alloys, silver-palladium alloys, nickel-chromium alloys, composite resins, acrylic resins, gold and gold alloys, porcelain, silver and silver alloys, alumina, zirconia, and other biocompatible materials, or combinations thereof.

The present invention provides the advantage of obtaining a superstructure allowing for a good fit of the superstructure to the gum, since the exact positioning of each integrated spacer has been calculated and thereafter fixed in the single-piece superstructure with integrated spacer(s). Also, the obtained superstructure, with integrated spacer(s) provides a simpler, faster and cheaper production method, since the superstructure and spacer(s) are manufactured in one piece. Thereby, eliminating costly manufacturing and assembling steps associated with the technique according to the prior art. Furthermore, a more simple assembly is obtained, since the person performing the assemblage not has to pay attention to a lot of different parts during assembly, which makes the assembly faster and simpler.

The superstructure with integrated spacer(s) may be manufactured to mimic the healing spacer(s) of an arbitrarily chosen dental implant system, whereby a good fit between the superstructure and the gum tissue may be obtained. It is also possible to mill the spacer(s) as straight cylinders, while still providing a superstructure with the advantages of allowing for a good fit of the superstructure to the gum, since the exact positioning of each integrated spacer has been calculated and thereafter fixed in the single-piece superstructure with integrated spacer(s), providing a simpler, faster and cheaper production method, since the superstructure and spacer(s) are manufactured in one piece, and providing a simpler assembly, since the person performing the assemblage not has to pay attention to a lot of different parts during assembly. An even further advantage with superstructure with integrated spacers is the spacer finish, where the surface can be made smooth and easy to polish.

Thus, the superstructure according to one embodiment of the invention comprises integrated spacer(s) with individually adapted dimension(s), angle(s) and shape(s). The information, in respect of the dimension(s), angle(s) and shape(s) of the spacer(s), may be specified by the dentist or dental technician prior to the manufacturing of the superstructure with integrated spacer(s).

One embodiment of the method of manufacturing of the superstructure, comprises the following steps:

1) The dental situation is obtained and/or determined. The obtainment of the dental situation can be performed in various ways known per se, for example by stereophotography, scanning of the outer form, etc, whereby a stereo-data is obtained. The scanning of the outer form can be performed using scanning needles, optical light beams, etc. The obtainment/determination of the dental situation may be performed before or after the application of healing spacer(s), which healing spacers may be obtained from any arbitrarily chosen dental implant system. The obtainment/determination of the dental situation may also be performed before or after the insertion of a dental implant in the bone tissue.

2) Information, in form of dimension(s), angle(s), and/or shape(s) of the spacer(s), at each position, is specified. This specification may be performed by a dentist or dental technician from a model of the dental situation of the patient. The specification may also be done automatically, such as through a computer software, using the stereo-data from step 1), which computer software may process the said stereo-data in accordance with predefined parameters to perform said specification. Said predefined parameters may for example be that a certain width of an integrated spacer will be chosen if the stereo-data reveals that there is a risk for increased stress on said integrated spacer.

3) This information is transferred or communicated to a computer. The transfer of the information may be performed or communicated manually or digitally.

4) The dental superstructure is produced through shaping of one single-piece blank from coordinate combinations calculated by said computer obtained from the preceding steps. Said shaping may be performed by any method selected from the group comprising milling, and moulding. In one embodiment of the present invention said shaping is performed by milling of a one single-piece blank, whereby a one single-piece superstructure with at least one integrated spacer is obtained.

The invention can be implemented in any suitable form including hardware, software, firmware or any combination of these. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

In yet another embodiment of the present invention the superstructure is provided with a dental implant seat or a spacer element seat, such as a recess suitable for receiving a protrusion on said dental implant or spacer element. It is of course also possible to provide the superstructure with a protrusion and the dental implant or spacer element with a recess, as long as the seating effect is obtained. This dental implant seat or a spacer element seat provides the advantage of easier assembling of the superstructure on a dental implant or a spacer element.

Although the present invention has been described above with reference to specific illustrative embodiments, it is not intended to be limited to the specific form set forth herein. Rather, the invention is limited only by the accompanying claims and other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method of manufacturing a dental superstructure having a plurality of integrated spacers, the method comprising:
   (a) obtaining stereo-data of a dental situation of a patient comprising dental implants that are osseointegrated in bone tissue;
   (b) specifying information from said stereo-data, said information comprising position, dimension, angle, and/or shape of said plurality of integrated spacers;
   (c) communicating said information and/or stereo-data to a computer; and
   (d) shaping said dental superstructure having said plurality of integrated spacers from a single-piece blank, from coordinate combinations calculated by said computer.

2. The method according to claim 1, wherein said obtaining stereo-data comprises obtaining by stereophotography or scanning.

3. The method according to claim 1, wherein said specifying information from said stereo-data is done automatically by a computer software.

4. The method according to claim 1, wherein said communicating is done manually or digitally.

5. The method according to claim 1, wherein said shaping is done on one single-piece blank to obtain a one single-piece superstructure with said plurality of integrated spacers.

6. The method according to claim 1, wherein said shaping is selected from the group consisting of milling and moulding.

7. The method according to claim 1, wherein each of said plurality of integrated spacer elements is dimensioned to cooperate with a corresponding one of said dental implants that are osseointegrated in bone tissue.

* * * * *